(12) United States Patent
Mark

(10) Patent No.: US 9,883,881 B2
(45) Date of Patent: Feb. 6, 2018

(54) MOTOR DRIVEN SURGICAL INSTRUMENT WITH FLUID CONTROL CIRCUIT

(75) Inventor: Joseph L. Mark, Indianapolis, IN (US)

(73) Assignee: NICO CORPORATION, Indianapolis, IN (US)

( * ) Notice: Subject to any disclaimer, the term of this patent is extended or adjusted under 35 U.S.C. 154(b) by 1039 days.

(21) Appl. No.: 13/485,494

(22) Filed: May 31, 2012

(65) Prior Publication Data

US 2013/0324976 A1 Dec. 5, 2013

(51) Int. Cl.
*A61B 17/32* (2006.01)
*A61B 17/00* (2006.01)
*A61B 90/00* (2016.01)

(52) U.S. Cl.
CPC .......... *A61B 17/32002* (2013.01); *A61B 2017/00017* (2013.01); *A61B 2017/00022* (2013.01); *A61B 2017/00039* (2013.01); *A61B 2017/00535* (2013.01); *A61B 2090/0811* (2016.02)

(58) Field of Classification Search
CPC .... A61B 17/32002; A61B 2017/00539; A61B 17/320016; A61B 2017/320024; A61B 2017/320028; A61B 2017/320032; A61B 2017/32004; A61B 2017/00535; A61B 2017/00022; A61B 2017/00017; A61B 2017/00039; A61F 9/00763
USPC ........................................................ 606/167
See application file for complete search history.

(56) References Cited

U.S. PATENT DOCUMENTS

| | | | |
|---|---|---|---|
| 3,924,335 A * | 12/1975 | Balamuth et al. | 433/119 |
| 4,345,192 A | 8/1982 | Kohzai et al. | |
| 4,705,038 A | 11/1987 | Sjostrom et al. | |
| 5,077,506 A | 12/1991 | Krause | |
| 5,269,794 A | 12/1993 | Rexroth | |
| 5,364,227 A | 11/1994 | Franetzki et al. | |
| 5,569,254 A | 10/1996 | Carlson et al. | |
| 5,669,921 A | 9/1997 | Berman et al. | |
| 5,672,945 A | 9/1997 | Krause | |
| 5,879,298 A | 3/1999 | Drobnitzky et al. | |
| 5,907,664 A | 5/1999 | Wang et al. | |
| 6,245,084 B1 | 6/2001 | Mark et al. | |
| 6,258,111 B1 | 7/2001 | Ross et al. | |
| 6,332,891 B1 | 12/2001 | Himes | |
| 6,358,263 B2 | 3/2002 | Mark et al. | |
| 7,617,826 B1 * | 11/2009 | Voege et al. | 128/204.26 |
| 7,648,466 B2 | 1/2010 | Stephens et al. | |
| 7,806,835 B2 | 10/2010 | Hibner et al. | |

(Continued)

OTHER PUBLICATIONS

PCT International Search Report, dated Sep. 5, 2013, in corresponding international patent application (filing date May 31, 2012).

*Primary Examiner* — Eric Rosen
*Assistant Examiner* — Chima Igboko
(74) *Attorney, Agent, or Firm* — Brooks Kushman, P.C.

(57) ABSTRACT

A surgical system includes a surgical tool having a motor with a shaft configured to rotate, a cutting device that reciprocates in accordance with the rotation of the shaft, and a position sensor that determines a state of the motor and outputs a position signal representing the motor state. A fluid regulator provides fluid to the motor, and the motor rotates in accordance with the fluid provided. A controller generates a fluid flow command based at least in part on the position signal. The fluid regulator receives the fluid flow command and regulates fluid flow to the motor accordingly.

20 Claims, 3 Drawing Sheets

(56) References Cited

U.S. PATENT DOCUMENTS

| | | |
|---|---|---|
| 8,230,859 B1 * | 7/2012 | Voege et al. ............. 128/204.26 |
| 2002/0108652 A1 * | 8/2002 | Palmer ......................... 137/497 |
| 2006/0173244 A1 | 8/2006 | Boulais et al. |
| 2006/0271242 A1 | 11/2006 | Shturman et al. |
| 2007/0232848 A1 * | 10/2007 | Forsell ............................ 600/31 |
| 2007/0260183 A1 | 11/2007 | Shores et al. |
| 2008/0145817 A1 * | 6/2008 | Brennan et al. ................ 433/98 |
| 2009/0143642 A1 | 6/2009 | Takahashi et al. |
| 2009/0240339 A1 | 9/2009 | Teitelbaum et al. |
| 2010/0152756 A1 * | 6/2010 | Mark .......................... 606/167 |

* cited by examiner

MOTOR DRIVEN SURGICAL INSTRUMENT WITH FLUID CONTROL CIRCUIT

TECHNICAL FIELD

The present disclosure relates to surgical devices, in particular, surgical devices that perform multiple functions and that are suited for neurosurgical and spinal surgical procedures.

BACKGROUND

Various abnormalities of the neurological system, such as brain and spinal tumors, cysts, lesions, or neural hematomas, can cause severe health risks to patients afflicted by them, including deterioration in motor skills, nausea or vomiting, memory or communication problems, behavioral changes, headaches, or seizures. In certain cases, resection of abnormal tissue masses is required. However, given the complexity and importance of the neurological system, such neurosurgical procedures are extremely delicate and must be executed with great precision and care.

DETAILED DESCRIPTION

Figure 1:
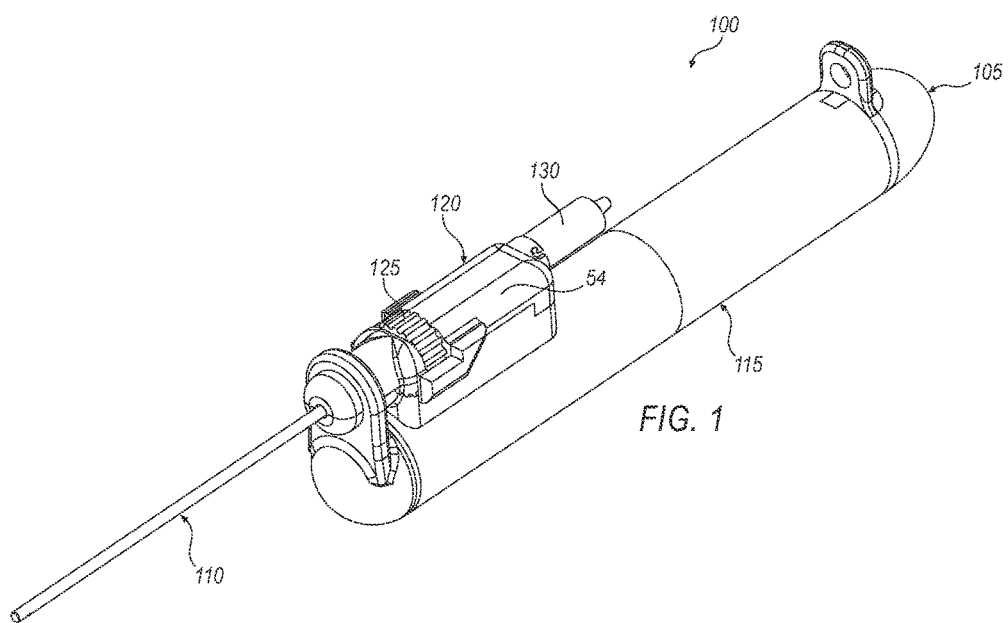
FIG. 1 is a perspective view of an example tissue cutting device in accordance with a first embodiment.

Referring now to the discussion that follows and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein is a system that includes a surgical tool that is suited for neurosurgical applications such as the removal of spine and brain tissue. In one example implementation, the surgical tool may include a motor having a shaft that rotates, a cutting device operably that reciprocates in accordance with the rotation of the shaft, and a position sensor that determines a state of the motor and outputs a position signal representing the determined state. The system may further include a fluid regulator in fluid communication with the motor and configured to provide fluid to the motor. The motor rotates in accordance with the fluid provided by the fluid regulator. Further, a controller is in communication with the position sensor and the fluid regulator. The controller generates a fluid flow command based at least in part on the position signal. The fluid regulator receives the fluid flow command and regulates fluid flow to the motor in accordance with the fluid flow command.

The exemplary controller described herein may eliminate variations between different motors. Some variations may include motor variability for start-up torque versus run torque as well as variations caused during the design and manufacturing process that are associated with different motor manufacturers. In addition, the controller may further reduce or eliminate variability that occurs with torque requirements of motors that change over time. Accordingly, the controller provides the ability for a fluid-based motor to operate with the same or similar level of control as a brushless electric motor while having the added benefit of MRI compatibility.

Referring to FIG. 1, a tissue cutting device 100 includes a handpiece 105 and a cannula assembly 110. In one exemplary implementation, the handpiece 105 is generally cylindrical in shape and is sized and shaped to be grasped with a single hand. The handpiece 105 includes a lower housing 115 and an upper housing 120. The lower housing 115 may, in one possible implementation, at least partially house elements such as a motor (see FIG. 4) while the upper housing 120 may at least partially house elements such as a rotation dial 125 for selective rotation of the cannula assembly 110 with respect to the handpiece 105. A tissue collector 130 may also be operationally attached to the upper housing 120 and configured to attach to a vacuum system (not shown) and aspirate tissue deposited during a tissue cutting procedure. While shown directly connected to the upper housing 120, the tissue collector 130 may alternatively be spaced away from the handpiece 105.

Figure 2:
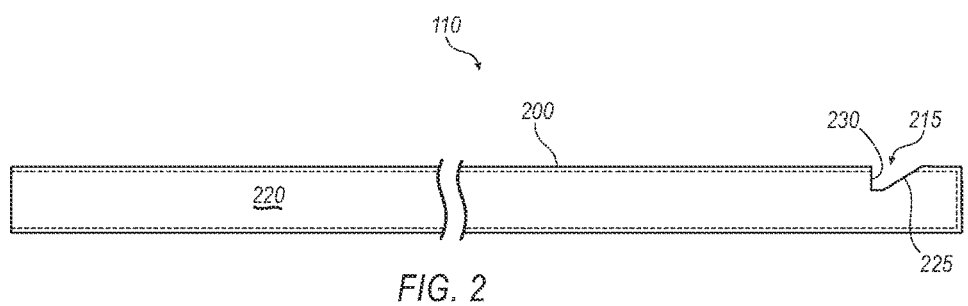
FIG. 2 is a broken side elevation view of the outer cannula of the tissue cutting device of FIG. 1.
Figure 3:
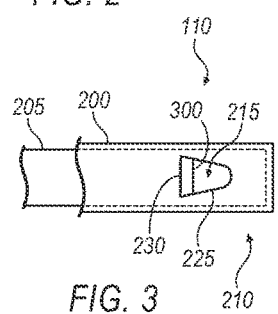
FIG. 3 is a top plan view of a portion of the outer cannula and inner cannula of FIG. 1 depicting the inner cannula inserted into the outer cannula

As illustrated in FIGS. 2 and 3, the cannula assembly 110 includes an outer cannula 200 and an inner cannula 205 that, when combined, form a cutting device 210. The outer cannula 200 may include an opening 215 for receiving tissue into an outer cannula lumen 220. The opening 215 is defined at least in part by a cutting edge 225, which is configured to sever tissue, and a non-cutting edge 230. In one possible approach, the cutting edge 225 may be beveled in a radially inward direction while the non-cutting edge 230 is not beveled. The cutting edge 225 may be further located immediately distally off the non-cutting edge 230.

Referring now to FIG. 3, a distal end 300 of the inner cannula 205 is configured to cut tissue. The distal end 300 may be beveled in a radially inward direction around the circumference of the inner cannula 205 to provide a sharp edge. During a tissue-cutting procedure, the inner cannula 205 reciprocates relative to the outer cannula 200. As tissue is received in the opening 215 of the outer cannula 200, it is compressed between the distal end 300 of the inner cannula 205 and the cutting edge 225 of the outer cannula 200, causing the received tissue to be severed from the surrounding tissue.

Figure 4:
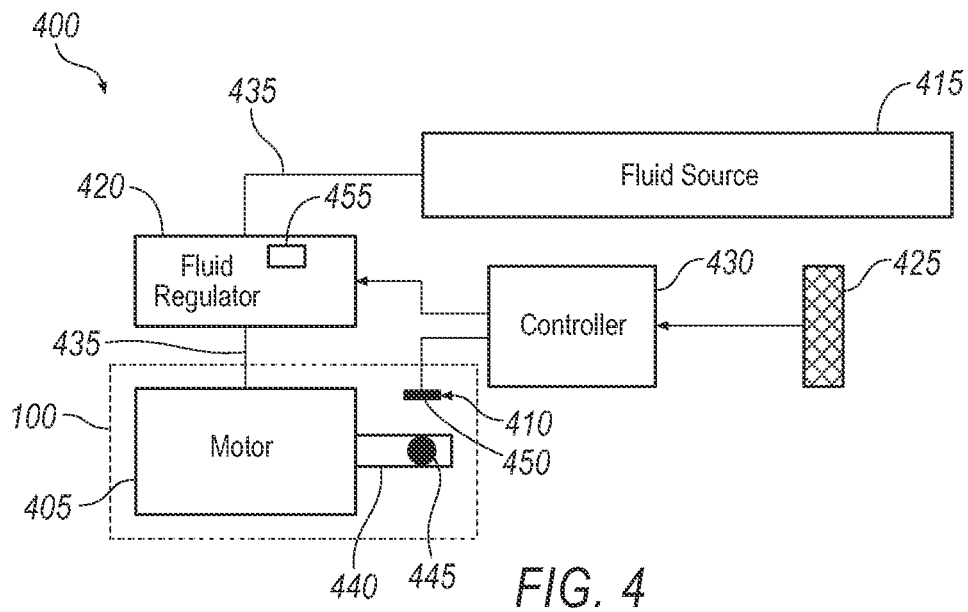
FIG. 4 is a block diagram of a control scheme for the tissue cutting system of FIG. 1.

FIG. 4 illustrates an exemplary block diagram of a surgical system 400 for controlling the operation of the tissue cutting device 100 of FIG. 1. The tissue cutting device 100, as illustrated in FIG. 4, includes a motor 405 and a position sensor 410. In addition to the tissue cutting device 100, the surgical system 400 further includes a fluid source 415, a fluid regulator 420, a footswitch 425, and a controller 430.

The motor 405 may include any hydraulically- or pneumatically-powered device configured to generate a torque when provided with an energy source such as pressurized fluid. Therefore, a hose 435 may provide fluid, such as air or water, to the motor 405. When provided with pressurized fluid, the motor 405 may generate a torque by rotating a shaft 440. The rotation of the shaft 440 may cause translational motion of the inner cannula 205 relative to the outer cannula 200 via a cam (not shown) or other device. The motor 405 may be housed in, e.g., the lower housing 115 section of the tissue cutting device 100.

The position sensor 410 may include any device configured to determine a state of the motor 405. For instance, the position sensor 410 may be configured to determine whether the motor 405 is rotating, the direction of the rotation, the speed of the rotation, etc. Because the movement of the inner cannula 205 relative to the outer cannula 200 is directly related to the rotation of the motor 405, the state of the motor 405 is indicative of the state of the cutting device 210.

In one possible approach, one or more magnets 445 may be disposed anywhere along the output shaft 440 of the motor 405, and the position sensor 410 may include a Hall Effect sensor 450. As the shaft 440 rotates, the magnet 445 moves relative to the Hall Effect sensor 450, and the strength of the magnetic field at various times may be registered by the Hall Effect sensor 450. The Hall Effect sensor 450 may be configured to output the position signal to indicate the position of the magnet 445 based, e.g., on the magnetic field. If the magnetic field strength remains constant, the position signal may represent that the shaft 440 is stationary (i.e., not rotating). If the magnetic field strength periodically cycles between maximum and minimum peak values, the position signal may represent that the shaft 440 is rotating, and the speed of the rotation may be determined from the frequency of the maximum or minimum peak values. The position signal may further indicate the position of the shaft 440 even when the shaft 440 is stationary (i.e., not rotating). For instance, the Hall Effect sensor 450 may be configured to determine the position of the shaft 440 based, at least in part, on the strength of the magnetic field. The position signal may therefore represent the state of the motor 405 based on, e.g., the position or movement of the magnet 445 relative to the Hall Effect sensor 450.

In some implementations, the position sensor 410 may be disposed outside of the handpiece 105 or possibly outside of the device 100. For instance, the magnet 445 may be disposed on a console remotely attached to the motor 405 via, e.g., a flexible shaft attached to the output shaft 440.

The fluid source 415 may include any structure configured to hold a volume of fluid, such as air or water, that may be used to drive the motor 405. The fluid source 415 may be configured to provide the fluid to the motor 405 either passively or actively via one or more hoses 435. For instance, to passively provide the fluid, the fluid source 415 may make the fluid available to be pumped or otherwise transmitted to the motor 405. Alternatively, the fluid source 415 may include a pump that may be controlled to actively provide pressurized fluid to the motor 405.

The fluid regulator 420 may include any device configured to provide the fluid from the fluid source 415 to the motor 405 via, e.g., one or more hoses 435. The fluid regulator 420 may be controlled to draw fluid from the fluid source 415 and to provide the fluid to the motor 405. In one possible approach, the fluid regulator 420 may include a pump 455 to pressurize the fluid before it is provided to the motor 405. Alternatively, the fluid may be pressurized in the fluid source 415, in which instance the fluid regulator 420 may act as a valve that provides the fluid to the motor 405. The fluid regulator 420 may be configured to operate in response to commands received from one or more electronic device, as discussed in further detail below. The received commands may indicate, for instance, the amount of fluid to provide to the motor 405, the pressure of the fluid to provide, the amount of fluid draw from the fluid source 415, or the like. Although shown as separate devices, the fluid source 415 and the fluid regulator 420 may be combined. That is, the fluid regulator 420 may include a pressurized fluid source so a separate fluid source 415 may not be necessary.

The footswitch 425 may include any device configured to allow a medical professional to control certain aspects of the operation of the surgical cutting device 100. In one possible approach, the footswitch 425 may be configured to generate and transmit an operation command representing a desired operation, such as a cutting operation, of the surgical cutting device 100. The footswitch 425 may include a pedal, and the medical professional may, using his or her foot, actuate the pedal to indicate a desire to begin the cutting operation (e.g., reciprocating the inner cannula 205 relative to the outer cannula 200). The distance that the pedal is actuated may indicate the desired speed of the motor 405 during the cutting operation. The operation command, therefore, may represent the desired speed of the motor 405, which as discussed above causes the movement of the inner cannula 205 relative to the outer cannula 200.

The controller 430 may include any device configured to receive the position signal from the position sensor 410 and the operation command from the footswitch 425 and generate a fluid flow command that may be used to regulate the fluid flow to the motor 405. That is, the controller 430 may be configured to generate the fluid flow command in accordance with the operation command and feedback, in the form of the position signal, from the position sensor 410. Using the fluid flow command, the controller 430 may regulate the speed of the motor 405, including holding the motor speed constant or varying the motor speed.

Because the controller 430 receives the state of the motor 405 from the position sensor 410 via the position signal, the controller 430 may be further configured to stop the rotation of the motor 405 at a predetermined position using the fluid flow command. In one example approach, when the medical professional lifts his or her foot off of the footswitch 425, the controller 430 may be configured to control the fluid flow to the motor 405 so that the shaft 440 will stop in a predefined position for example one configuration is where the inner cannula 205 does not block the opening 215 in the outer cannula 200. For instance, the controller 430 may cause the motor speed to slow after the medical professional lifts his or her foot off of the footswitch 425. While at the slowed speed, the controller 430 may continue to monitor the position of the shaft 440 as indicated by the position signal. When the shaft 440 is in a particular position, the controller 430 may output a fluid flow command to the fluid regulator 420 that ultimately causes the motor 405 to stop the rotation of the shaft 440. After accounting for delays in transmitting the fluid flow command and the response time of the motor 405, the controller 430 may, using the fluid flow command, cause the shaft 440 of the motor 405 to stop in a desired position.

The controller 430 may be configured to control the fluid flow to the motor 405 using a predetermined set of instructions. Instructions may, for instance, call for the controller 430 to output a fluid flow command that causes the speed of the motor 405 to pulse or alternatively causes the speed of the motor 405 to be held relatively constant. It is further possible for the controller 430, using the fluid flow command, to provide an initial burst of fluid to the motor 405 to cause the motor 405 to begin rotating. Such burst of fluid may help overcome any static friction of the motor 405. Additionally, the set of instructions may cause the controller 430 to output a sequence of fluid flow commands that may cause the motor speed to follow a predetermined sequence of responses. Such sequence may include any combination of the following actions for one or more predetermined amounts of time: increasing the motor speed, decreasing the motor speed, maintaining a constant motor speed, pulsing the motor speed, or stopping the shaft 440 of the motor 405 at a predetermined position.

Figure 5:
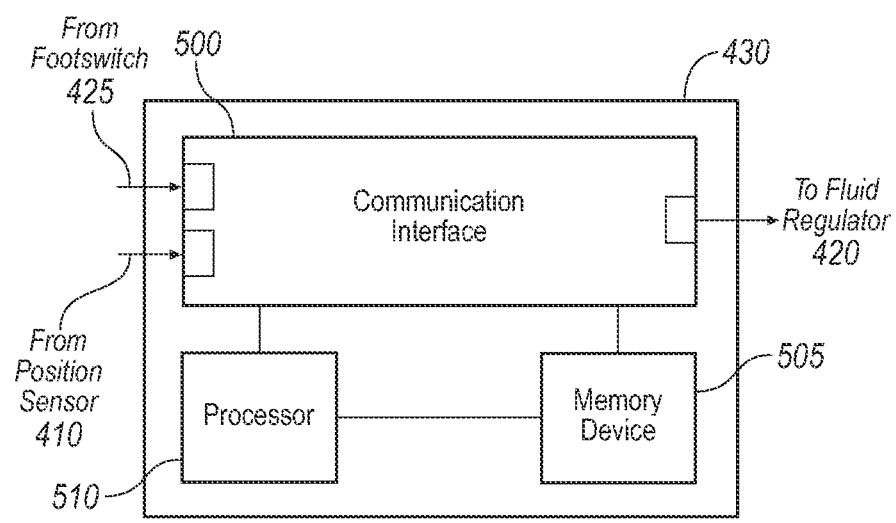
FIG. 5 is a block diagram of an example controller that may be used in the tissue cutting system of FIG. 1.

FIG. 5 is a block diagram of an example controller 430. As illustrated in FIG. 5, the controller 430 may include a communication interface 500, a memory device 505, and a processor 510.

The communication interface 500 may include any number of devices configured to receive various commands and signals. For instance, the communication interface 500 may be configured to receive the operation command from the footswitch 425 and the position signal from the position sensor 410. Further, the communication interface 500 may further allow for the controller 430 to output commands or signals to other devices. In one possible approach, the communication interface 500 may therefore transmit the fluid flow command to the fluid regulator 420.

The memory device 505 may include any device configured to electronically store information. The memory device 505 may include any number of volatile memory devices, non-volatile memory devices, or any combination thereof. The memory device 505 may store one or more predetermined sets of instructions that may be used to generate the fluid flow command.

The processor 510 may include any device configured to process various commands, signals, or both, and generate a fluid flow command. The processor 510 may be configured to receive commands, signals, or both, from the communication interface 500. For example, the processor 510 may be configured to access, via the communication interface 500, the operation command generated by the footswitch 425 and the position signal generated by the position sensor 410. The processor 510 may be further configured to generate the fluid flow command based, at least in part, on any received commands or signals, which may include the operation command and the position signal. Once generated, the processor 510 may be configured to transmit the fluid flow command to the communication interface 500 so that the fluid flow command may be transmitted to, e.g., the fluid regulator 420.

During operation of the surgical system 400, that is, when the pedal of the footswitch 425 is initially actuated, the footswitch 425 may generate the operation command and transmit the operation command to the controller 430. The controller 430 may, in accordance with the operation command, generate a fluid flow command that causes fluid to flow from the fluid source 415 to the motor 405. The controller 430 may transmit the fluid flow command to the fluid regulator 420, and the fluid regulator 420 may facilitate the flow of fluid from the fluid source 415 to the motor 405 in accordance with the fluid flow command. In one possible approach, the fluid flow command may instruct the fluid regulator 420 to provide the motor 405 with an initial burst of fluid that is greater than typically needed to drive the motor 405. This initial burst of fluid may be used, e.g., to overcome the static friction of the motor 405. The controller 430 may subsequently increase, decrease, or maintain the speed of the motor 405 based either on the operation command or in accordance with a set of instructions stored in the memory of the controller 430. To do so, the controller 430 may transmit subsequent fluid flow commands to the fluid regulator 420. In addition to the operation command, the fluid flow commands generated by the controller 430 may further consider the current state of the motor 405 identified by the position signal.

In some instances, the controller 430 may continue to transmit fluid flow commands even after the footswitch 425 is not actuated. That is, when the medical professional lifts his or her foot off of the pedal, the controller 430 may transmit a fluid flow command that causes the motor speed to slow. Using the feedback provided by the position signal, the controller 430 may further generate a fluid flow command that causes the shaft 440 to stop at a particular position. The fluid flow commands associated with slowing and stopping of the motor 405 may be based on instructions stored in the memory.

In general, computing systems and/or devices, such as the controller 430, may employ any of a number of computer operating systems, including, but by no means limited to, versions and/or varieties of the Microsoft Windows® operating system, the Unix operating system (e.g., the Solaris® operating system distributed by Sun Microsystems of Menlo Park, California), the AIX UNIX operating system distributed by International Business Machines of Armonk, N.Y., and the Linux operating system. Examples of computing devices include, without limitation, a computer workstation, a server, a desktop, notebook, laptop, or handheld computer, or some other known computing system and/or device.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of known computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners, as is known. A file system may be accessible from a computer operating system, and may include files stored in various formats. An RDBMS generally employs the Structured Query Language (SQL) in addition to a language for creating, storing, editing, and executing stored procedures, such as the PL/SQL language.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be apparent upon reading the above description. The scope of the invention should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the invention is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A surgical system comprising:
   a surgical tool having a fluidic motor with a shaft configured to rotate, a cutting device operably connected to the motor and configured to reciprocate in response to the rotation of the shaft, and a position sensor located in a housing of the surgical tool and configured to determine a state of the motor and output a position signal representing the state of the motor;
   a fluid regulator in fluid communication with the motor and configured to provide fluid to the motor; and
   a controller in communication with the position sensor and the fluid regulator and configured to generate a fluid flow command based at least in part on the position signal and an operation command,
   wherein the fluid regulator is configured to receive the fluid flow command and regulate fluid flow to the motor in accordance with the fluid flow command, and wherein the shaft of the motor is configured to rotate in accordance with the fluid flow provided by the fluid regulator.

2. A surgical system as set forth in claim 1, wherein the surgical tool includes a magnet disposed on the shaft of the motor, and wherein the position sensor includes a Hall Effect sensor configured to determine the position of the shaft based at least in part on a position of the magnet relative to the Hall Effect sensor.

3. A surgical system as set forth in claim 1, further comprising a fluid source, and wherein the fluid regulator is configured to receive fluid from the fluid source in accordance with the fluid flow command.

4. A surgical system as set forth in claim 1, further comprising a fluid source, and wherein the fluid regulator includes a pump configured to draw fluid from the fluid source and to provide the fluid to the motor in accordance with the fluid flow command.

5. A surgical system as set forth in claim 1, further comprising a footswitch configured to output the operation command, and wherein the controller is configured to receive the operation command from the footswitch and generate the fluid flow command based at least in part on the operation command.

6. A surgical system as set forth in claim 1, wherein the controller is configured to regulate a speed of the motor via the fluid flow command.

7. A surgical system as set forth in claim 1, wherein the controller is configured to vary a speed of the motor via the fluid flow command.

8. A surgical system as set forth in claim 1, wherein the controller is configured to stop the rotation of the motor in a predetermined position via the fluid flow command.

9. A surgical system as set forth in claim 1, wherein the controller is configured to pulse a speed of the motor via the fluid flow command.

10. A surgical system as set forth in claim 1, wherein the fluid regulator is configured to provide a burst of fluid to the motor to cause the motor to begin rotating in accordance with the fluid flow command.

11. A surgical system as set forth in claim 1, wherein the controller is configured to generate the fluid flow command based at least in part on a predetermined set of instructions associated with a desired motor speed.

12. A surgical system as set forth in claim 1, wherein the motor includes at least one of a hydraulic motor and a pneumatic motor.

13. A surgical system comprising:
    a fluid source configured to hold a fluid;
    a footswitch having a pedal and configured to generate an operation command based at least in part on the position of the pedal;
    a surgical tool having a motor configured to rotate, a fluid regulator configured to draw fluid from the fluid source and provide the fluid to the motor, and a position sensor configured to generate a position signal indicating a state of the motor; and a controller in communication with the footswitch and the surgical tool and configured to generate a fluid flow command based at least in part on the operation command and the position signal, wherein the fluid regulator is configured to provide fluid to the motor in accordance with the fluid flow command generated by the controller.

14. A surgical system as set forth in claim 13, wherein the motor includes a shaft and the surgical tool further includes a magnet disposed on the shaft of the motor, and wherein the position sensor includes a Hall Effect sensor configured to determine the position of the shaft based at least in part on a position of the magnet relative to the Hall Effect sensor.

15. A surgical system as set forth in claim 13, wherein the fluid regulator includes a pump configured to draw fluid from the fluid source and to provide the fluid to the motor in accordance with the fluid flow command.

16. A surgical system as set forth in claim 13, wherein the controller is configured to regulate the speed of the motor via the fluid flow command.

17. A surgical system as set forth in claim 13, wherein the controller is configured to vary a speed of the motor via the fluid flow command.

18. A surgical system as set forth in claim 13, wherein the controller is configured to stop the rotation of the motor in a predetermined position via the fluid flow command.

19. A surgical system as set forth in claim 13, wherein the controller is configured to pulse a speed of the motor via the fluid flow command.

20. A controller for a surgical cutting tool, the controller comprising:

a communication interface configured to receive an operation command from a footswitch and a position signal from a position sensor; and a processor configured to generate a fluid flow command based at least in part on the operation command and the position signal, wherein the communication interface is further configured to output the fluid flow command to a fluid regulator to control operation of a motor.

* * * * *